(12) United States Patent
Thompson, Jr. et al.

(10) Patent No.: US 10,537,448 B2
(45) Date of Patent: *Jan. 21, 2020

(54) BIO-MECHANICAL PROSTHETIC FINGER WITH H-SHAPED ROCKER

(71) Applicant: RCM Enterprise, LLC, Olympia, WA (US)

(72) Inventors: Robert Thompson, Jr., Olympia, WA (US); Jon Bengtsson, Olympia, WA (US); Anthony Charles Peto, Olympia, WA (US); Charles Colin Macduff, Olympia, WA (US); Sydney Tye Minnis, Seattle, WA (US); Eric Dennis Klumper, Boulder, CO (US); Bradley Arthur Crittenden, Olympia, WA (US)

(73) Assignee: RCM Enterprise LLC, Olympia, WA (US)

( * ) Notice: Subject to any disclaimer, the term of this patent is extended or adjusted under 35 U.S.C. 154(b) by 8 days.

This patent is subject to a terminal disclaimer.

(21) Appl. No.: 15/986,411

(22) Filed: May 22, 2018

(65) Prior Publication Data
US 2018/0280160 A1    Oct. 4, 2018

Related U.S. Application Data

(60) Division of application No. 15/590,684, filed on May 9, 2017, now Pat. No. 9,999,521, which is a
(Continued)

(51) Int. Cl.
*A61F 2/58* (2006.01)
*A61F 2/76* (2006.01)
*A61F 2/50* (2006.01)

(52) U.S. Cl.
CPC ............ *A61F 2/5046* (2013.01); *A61F 2/586* (2013.01); *A61F 2/76* (2013.01);
(Continued)

(58) Field of Classification Search
CPC .... A61F 2/54; A61F 2/58; A61F 2/586; A61F 5/01; A61F 2/76
See application file for complete search history.

(56) References Cited

U.S. PATENT DOCUMENTS

| 319,776 A | 6/1885 | Bashore |
| 984,179 A | 2/1911 | Aydt |

(Continued)

FOREIGN PATENT DOCUMENTS

| GB | 2488365 | 8/1912 |
| GB | 108872 | 8/1917 |

(Continued)

OTHER PUBLICATIONS

Pop, S., "Finger Prosthetic Shows Perfect Balance Between Flexibility and Sturdiness—Gallery", Oct. 23, 2014, 8 pp. as downloaded on Jul. 12, 2017.

(Continued)

*Primary Examiner* — Bruce E Snow
(74) *Attorney, Agent, or Firm* — James A. Sheridan; Sheridan Law, LLC

(57) ABSTRACT

The disclosure provides apparatus and methods of use pertaining to a prosthetic finger assembly. In one embodiment, the assembly includes a coupling tip and a distal ring coupled with the coupling tip. The assembly further includes a proximal ring coupled with the distal ring. A rocker formed in an H-shape with a first end forming a first split prong and a second end forming a second split prong may extend between the coupling tip and the proximal ring. The coupling tip, distal ring, proximal ring, and H-shaped rocker may all be hingedly connected such that movements of the residual finger within the proximal ring articulate the distal ring together with the rocker to articulate the coupling tip. Other embodiments are also disclosed.

13 Claims, 11 Drawing Sheets

Related U.S. Application Data continuation of application No. 15/013,891, filed on Feb. 2, 2016, now Pat. No. 9,707,102.

(60) Provisional application No. 62/111,464, filed on Feb. 3, 2015, provisional application No. 62/209,843, filed on Aug. 25, 2015.

(52) U.S. Cl.
CPC . *A61F 2002/5001* (2013.01); *A61F 2002/505* (2013.01); *A61F 2002/5083* (2013.01); *A61F 2220/0091* (2013.01)

(56) References Cited

U.S. PATENT DOCUMENTS

| | | | |
|---|---|---|---|
| 2,598,593 A | 5/1952 | Parker | |
| 2,706,296 A | 4/1955 | Fletcher | |
| 2,876,819 A | 1/1959 | George | |
| 3,483,718 A | 12/1969 | Lodrini | |
| 3,707,963 A | 1/1973 | Keropian | |
| 4,258,441 A | 3/1981 | Bell | |
| 4,813,406 A | 3/1989 | Ogle, II | |
| 4,997,433 A | 3/1991 | Goble et al. | |
| 5,062,855 A | 11/1991 | Rincoe | |
| 5,941,914 A | 8/1999 | Jacobsen et al. | |
| 6,416,703 B1 | 7/2002 | Kristinsson et al. | |
| 6,481,114 B1 * | 11/2002 | Kalajian | A44C 9/02 33/512 |
| 6,908,489 B2 * | 6/2005 | Didrick | A61F 2/586 623/64 |
| 8,337,568 B2 | 12/2012 | Macduff | |
| 9,375,319 B2 | 6/2016 | Macduff | |
| 9,629,731 B2 | 4/2017 | Thompson et al. | |
| 9,707,101 B2 | 7/2017 | Thompson et al. | |
| 9,707,103 B2 | 7/2017 | Thompson, Jr. et al. | |
| 9,713,541 B2 | 7/2017 | Thompson et al. | |
| 9,849,001 B2 | 12/2017 | Thompson et al. | |
| 9,949,847 B2 | 4/2018 | Thompson et al. | |
| 10,016,289 B2 | 7/2018 | Thompson et al. | |
| 10,022,248 B2 | 7/2018 | Thompson, Jr. et al. | |
| 10,123,885 B2 * | 11/2018 | Thompson, Jr. | A61F 2/586 |
| 10,327,921 B2 * | 6/2019 | Thompson, Jr. | A61F 2/586 |
| 2004/0054424 A1 | 3/2004 | Matsuda | |
| 2005/0043822 A1 | 2/2005 | Didrick | |
| 2006/0212129 A1 | 9/2006 | Lake et al. | |
| 2006/0224249 A1 | 10/2006 | Winfrey | |
| 2008/0127768 A1 | 6/2008 | Shirai et al. | |
| 2008/0262636 A1 | 10/2008 | Puchhammer | |
| 2010/0042229 A1 | 2/2010 | Hawk | |
| 2010/0082103 A1 | 4/2010 | Blunn | |
| 2010/0191343 A1 | 7/2010 | Puchammer et al. | |
| 2010/0262057 A1 | 10/2010 | Chandrasekhar et al. | |
| 2011/0144770 A1 | 6/2011 | Moyer et al. | |
| 2011/0208322 A1 | 8/2011 | Rifkin, Jr. et al. | |
| 2012/0109337 A1 | 5/2012 | Schulz | |
| 2012/0146352 A1 | 6/2012 | Haslinger | |
| 2012/0303136 A1 | 11/2012 | Macduff | |
| 2012/0330432 A1 | 12/2012 | Fong | |
| 2013/0226315 A1 | 8/2013 | Varley | |
| 2013/0268094 A1 | 10/2013 | Van Wiemeersch | |
| 2014/0078118 A1 | 3/2014 | Robb | |
| 2014/0202741 A1 | 10/2014 | Macduff | |
| 2014/0303741 A1 | 10/2014 | Macduff | |
| 2014/0303749 A1 | 10/2014 | Macduff | |
| 2014/0303750 A1 | 10/2014 | Macduff | |
| 2014/0371897 A1 | 12/2014 | Lin et al. | |
| 2015/0138968 A1 | 9/2015 | Hunter | |
| 2017/0181870 A1 | 6/2017 | Thompson et al. | |
| 2018/0200080 A1 | 7/2018 | Thompson et al. | |
| 2018/0243109 A1 | 8/2018 | Thompson et al. | |

FOREIGN PATENT DOCUMENTS

| | | |
|---|---|---|
| GB | 110333 | 10/1917 |
| JP | 2002345861 | 12/2002 |
| WO | 2007/076765 A2 | 7/2008 |
| WO | 2010/095619 A1 | 8/2010 |
| WO | 2016/126732 | 8/2016 |
| WO | 2016/126736 | 8/2016 |
| WO | 2016/126739 | 8/2016 |
| WO | 2016/187133 | 11/2016 |
| WO | 2016187127 | 11/2016 |
| WO | 2017/035387 | 3/2017 |

OTHER PUBLICATIONS

International Search Report and Written Opinion dated Nov. 4, 2016 for Int. Appl. No. PCT/US16/48758, 7 pp.
International Search Report and Written Opinion dated Jun. 10, 2016 for Int. Appl. No. PCT/US16/16219, 6 pp.
International Search Report and Written Opinion dated Jun. 2, 2016 for Int. Appl. No. PCT/US16/16223, 12 pp.
Leow, M., et al. "Optimal Circumference Reduction of Finger Models for Good Prosthetic Fit of a Thimble-Type Prosthesis for Distal Finger Amputations", Journal of Rehabilitation Research and Development, Mar. 2001, vol. 38, No. 2; pp. 273-279.
Cabibihan, J., "Patient-Specific Prosthetic Fingers by Remote Collaboration—a Case Study", PLoS ONE, May 2011, vol. 6, No. 5.
International Search Report and Written Opinion dated Apr. 22, 2016 for Int. Appl. No. for PCT/US16/16215, 8 pp.
International Search Report and Written Opinion dated Aug. 25, 2016 for Int. Appl. No. PCT/US16/32732, 11 pp.
International Search Report and Written Opinion dated Aug. 26, 2016 for Int. Appl. No. PCT/US16/32721, 21 pp.

* cited by examiner

BIO-MECHANICAL PROSTHETIC FINGER WITH H-SHAPED ROCKER

REFERENCE TO PENDING PRIOR PATENT APPLICATION

This application is a divisional of U.S. patent application Ser. No. 15/590,684, filed May 9, 2017 by Robert Thompson Jr., Jon Bengtsson, Charles Colin Macduff, Anthony Charles Peto, Sydney Tye Minnis, Eric Dennis Klumper, and Bradley Arthur Crittenden for "BIO-MECHANICAL PROSTHETIC FINGER WITH H-SHAPED ROCKER," which is a divisional of U.S. patent application Ser. No. 15/013,891, filed Feb. 2, 2016 by Robert Thompson Jr., Jon Bengtsson, Charles Colin Macduff, Anthony Charles Peto, Sydney Tye Minnis, Eric Dennis Klumper, and Bradley Arthur Crittenden for "BIO-MECHANICAL PROSTHETIC FINGER WITH H-SHAPED ROCKER," which application issued as U.S. Pat. No. 9,707,102 on Jul. 18, 2017, and which application claims the benefit under 35 U.S.C. 119 (e) of U.S. Provisional Patent Application Nos. 62/111,464, filed Feb. 3, 2015 by Jon Bengtsson, Robert Thompson, and Charles Colin Macduff for "BIO-MECHANICAL PROSTHETIC FINGER WITH H-SHAPED ROCKER," and 62/209,843, filed Aug. 25, 2015 by Robert Thompson, Jr., Jon Bengtsson, Anthony Charles Peto, Sydney Tye Minnis, Eric Dennis Klumper, and Bradley Arthur Crittenden for "BIO-MECHANICAL PROSTHETIC FINGER WITH H-SHAPED ROCKER," all of which patent applications are hereby incorporated herein by reference.

BACKGROUND

If a person loses a finger, a finger segment, or a fingertip, the result is impaired performance of the hand. Having an amputated finger inhibits an amputee from performing some of the most basic tasks. For example, with a lost finger or fingertip, the task of typing on a computer keyboard or dialing on a telephone becomes significantly more difficult. These types of tasks require precise actions that only fingers are able to offer.

Not only do they allow for the performance of precise physical actions, fingers also provide an increased ability to grip or handle items. While holding an item in the hand, the weight of the item is dispersed through all of a user's fingers. By varying the force used by each finger on the holder's hand, the holder is able to manipulate the item in a myriad of ways. However, if the holder is missing all or even part of a single digit, or if a digit is present but nonfunctioning, this freedom of manipulation and the number of degrees through which the holder can manipulate the item is drastically decreased.

Current prosthetic finger solutions demonstrate several drawbacks. First, a primary category of prosthetic fingers offers only cosmetic restoration. These prosthetics are designed to be worn passively and offer a realistic look. They provide little to no functionality and do not enable the owner to restore functionality to his or her hand. Other prosthetics offer the user some level of restored functionality, but are complex in design and electrically powered. These prosthetics, while perhaps better than going without, are impractical in that they require an external power source and can be both bulky and unwieldy for the user to manage. Still other prosthetic fingers are body-powered but lack the design flexibility necessary to accommodate any length of residual finger (e.g., all or partially amputated and varying degrees of amputation) while providing maximum dexterity, grip strength, and finger articulation.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a biomechanically driven prosthetic finger assembly. The biomechanically driven prosthetic finger assembly includes (1) a distal ring rotatively coupled between a coupling tip and a proximal ring via respective first and second hinged connections; and (2) a rocker rotatively coupled between the coupling tip and the proximal ring via respective third and fourth hinged connections. The first and second hinged connections may define a midline relative to a z-axis, where the third hinged connection is located below the midline and the fourth hinged connection is located above the midline, such that a relative rotational motion between the proximal ring and the distal ring causes a relative rotational motion between the distal ring and the coupling tip to emulate a finger's natural closing motion.

Another embodiment provides a method of fitting a customized prosthetic finger having a proximal ring configured to anchor to a patient's residual finger, where the proximal ring contains one or more shim-retainment apertures. The method begins with inserting the residual finger into an interior of the proximal ring of the prosthetic finger and continues with assessing a tightness of the proximal ring about the residual finger. Next, the method includes selecting a first shim having a first thickness from a plurality of shims configured to line the interior of the proximal ring, each of the shims including one or more retaining grommets, and removing the residual finger from the proximal ring. Then the method involves inserting the first shim into the interior of the proximal ring such that the retaining grommets protrude through the shim-retainment apertures, thereby retaining the first shim within the interior of the proximal ring, before reinserting the residual finger.

The method discussed above may further include assessing a tightness of the first shim about the residual finger, and then removing the residual finger and the first shim before selecting, from the plurality of shims, a second shim having a second thickness. Once the second shim is selected, the user may continue by inserting the second shim into the interior of the proximal ring such that the retaining grommets protrude through the shim-retainment apertures, thereby retaining the second shim within the interior of the proximal ring.

Yet another embodiment provides a prosthetic finger device. The prosthetic finger device includes (1) a distal linkage rotatively coupled with a proximal linkage; (2) a rocker structure rotatively coupled between a receiving tip and the proximal linkage; (3) a proximal cage ring attached to the proximal linkage; and (4) a distal cage ring attached to the distal linkage. The proximal and distal cage rings are configured to anchor onto a user's residual finger in a manner that nests an end of the residual finger within the receiving tip such that movement of the residual finger within the proximal and distal cage rings articulates the distal and proximal linkages together with the rocker to articulate the receiving tip. The proximal cage ring may be interchangeable with a plurality of replacement proximal cage rings having varying diameters, and the distal cage ring may be interchangeable with a plurality of replacement distal cage rings having varying diameters.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments disclosed herein relate to a custom-designed, self-contained prosthetic finger that can be fitted for a user with an amputated finger, fingertip, or finger segment. The streamlined, sophisticated, and biomechanically driven design allows for a patient with any level of residual finger to utilize a mechanical replacement that mimics the motions and functionalities of a real finger. The natural action of the prosthetic finger assembly allows users to regain maximum control of the flexion and extension movements of a full finger and fingertip and is designed to bend and curl in a realistic, natural manner in response to movement in the user's residual finger or adjacent fingers.

Embodiments described herein feature specially designed components, such as an H-shaped rocker and/or a cupped receiving tip, both discussed in detail below, that allow the prosthetic finger to anchor to any length of residual finger, while protecting the amputation site against further injury or hypersensitivity and providing the individual user with maximum fit and use flexibility, dexterity, grip strength, and articulation. As a result, the prosthetic finger offers digit amputees a functional solution that eases the transition back into daily activities, no matter how intricate, after amputation.

Figure 1:
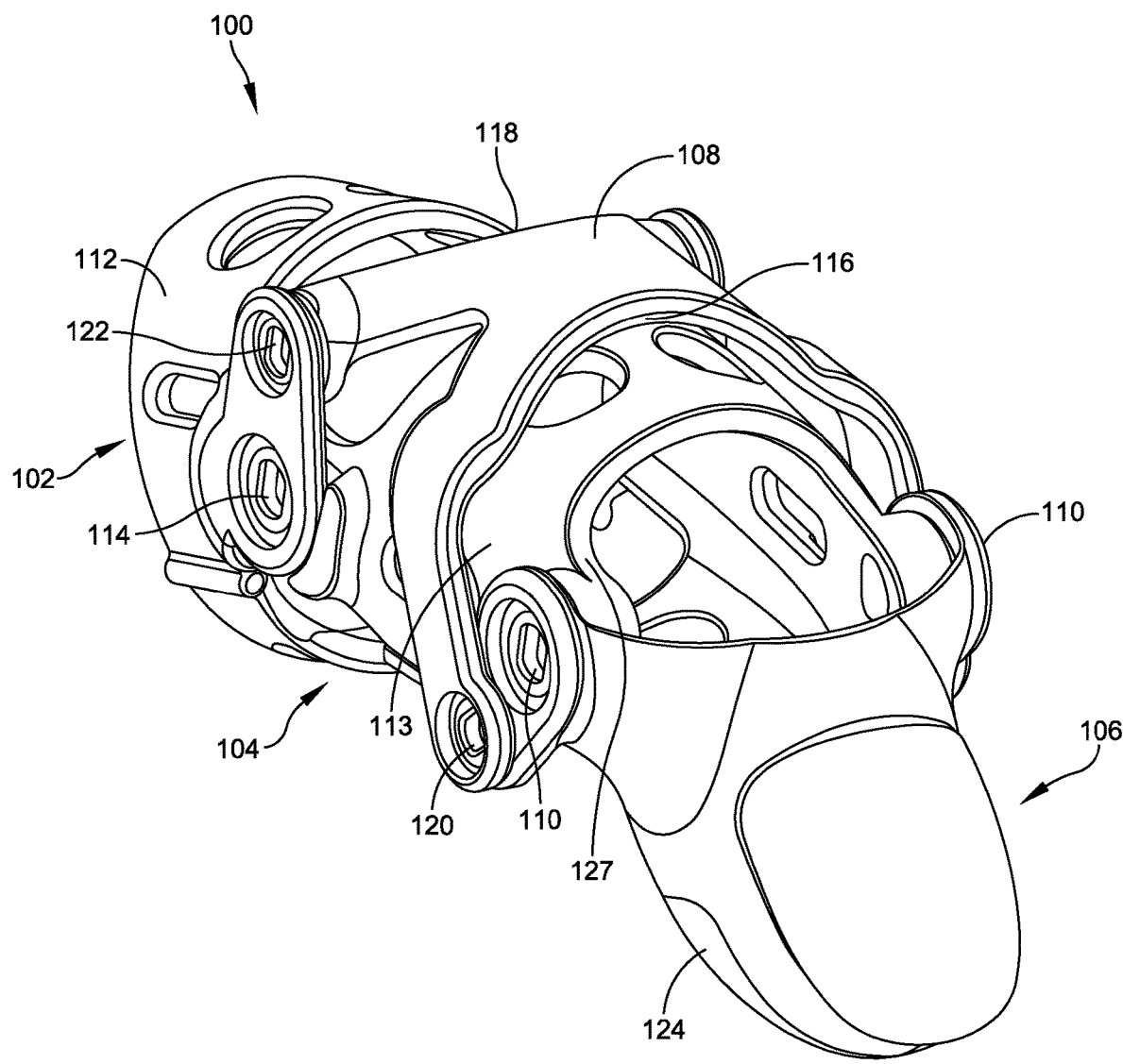
FIG. 1 illustrates a perspective view of one embodiment of a prosthetic finger assembly featuring an H-shaped rocker.
Figure 2:
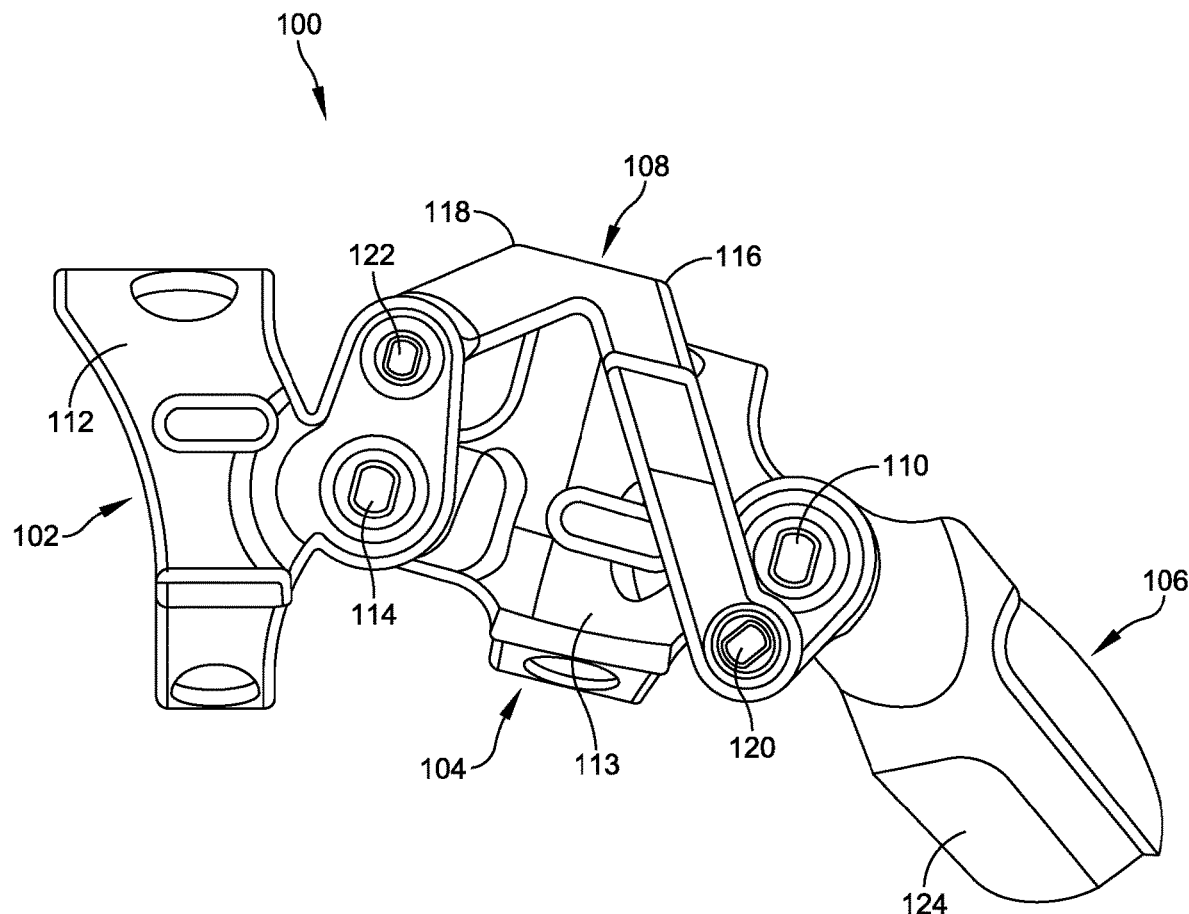
FIG. 2 illustrates a left-side elevation view of the prosthetic finger assembly of FIG. 1.
Figure 3:
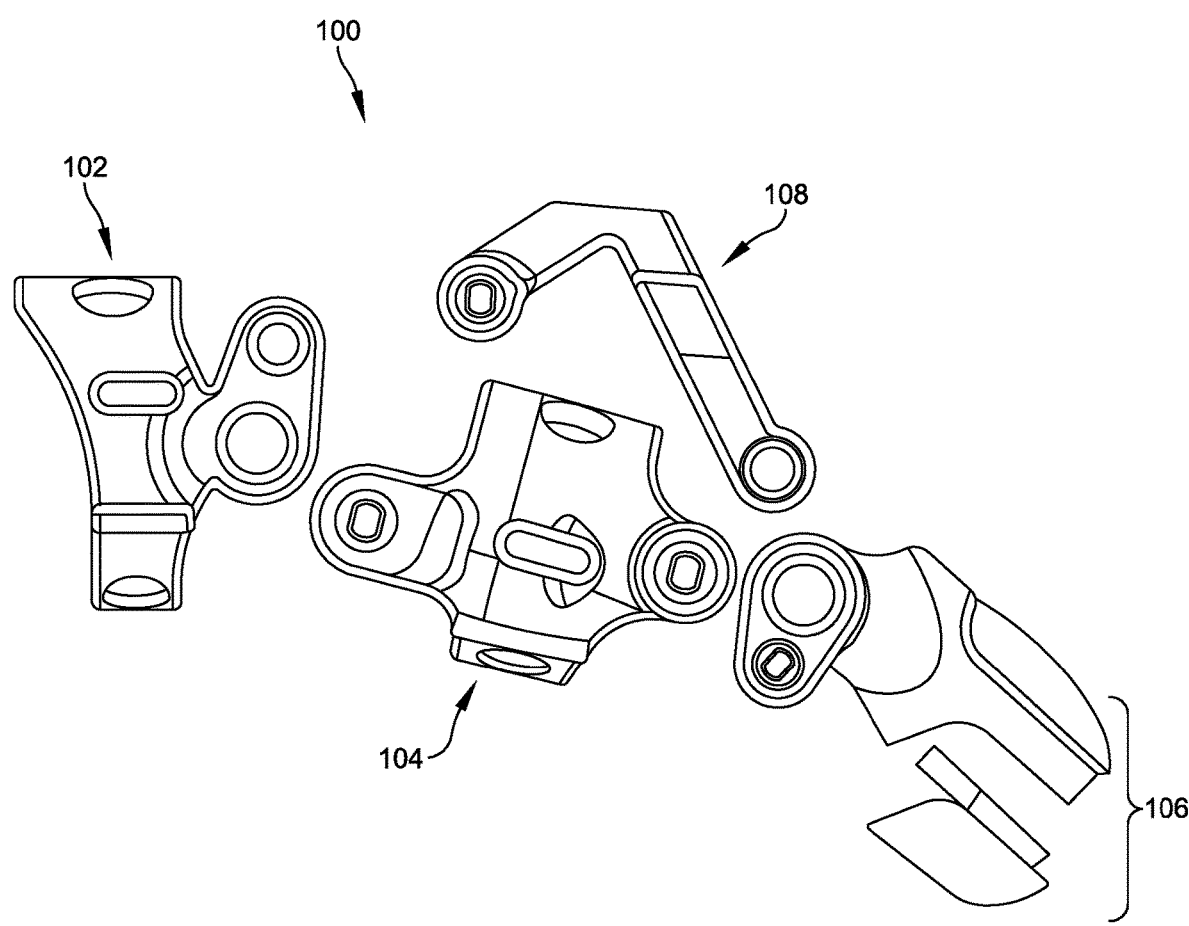
FIG. 3 illustrates an exploded view of the prosthetic finger assembly of FIGS. 1 and 2.

FIGS. 1-3 illustrate perspective, side, and exploded views of one embodiment of a prosthetic finger 100. In this embodiment, prosthetic finger 100 may include four major interconnected components that extend from a proximal end located at the patient's hand to a distal end located at a distance from the patient's hand. These components include a proximal ring 102, a distal ring 104, a coupling tip 106, and an H-shaped rocker 108. Proximal ring 102 and distal ring 104 may each have a respective body 112, 113. In this embodiment, bodies 112, 113 may form circular or ring shapes that are configured to anchor onto a patient's/user's residual finger. More specifically, body 112 of proximal ring 102 may be configured to anchor about a proximal phalanx of a user's residual finger with a snug fit. Similarly, body 113 of distal ring 104 may be configured to anchor about a middle phalanx of a user's residual finger with a snug fit.

Figure 4:
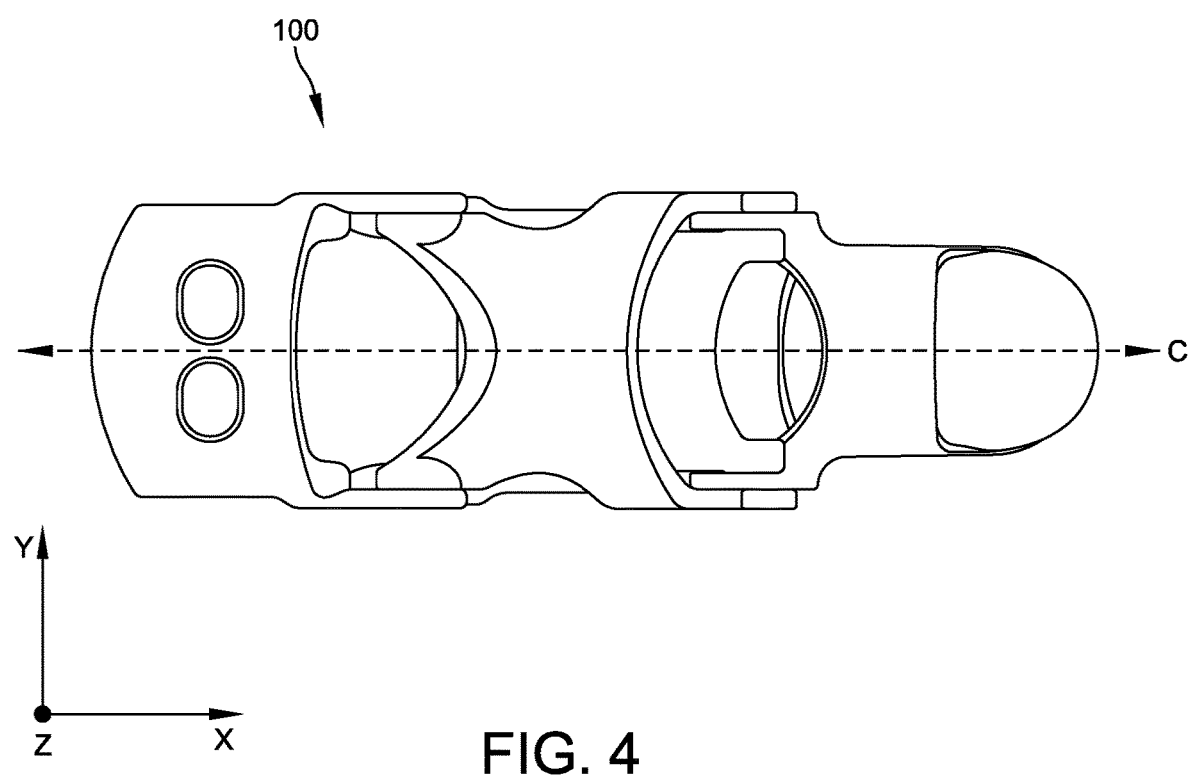
FIG. 4 illustrates a top view of the prosthetic finger assembly of FIGS. 1-3, with a centerline axis bisecting the assembly relative to a y-axis.
Figure 5:
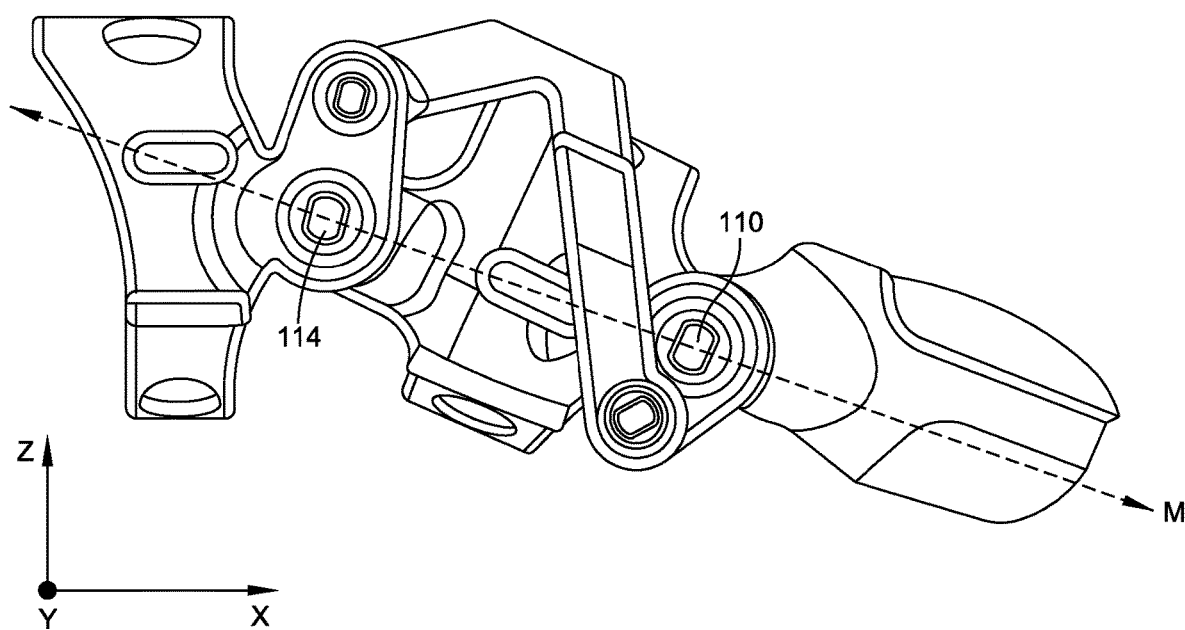
FIG. 5 illustrates another left-side view of the prosthetic finger assembly of FIGS. 1-4, with a midline axis intersecting first and second hinged connections relative to a z-axis.

A series of hinges may be used to secure the four primary components discussed above via rotative connections. In one embodiment, these rotative connections may be particularly positioned with respect to a pair of axes detailed in FIGS. 4-5. More specifically, FIG. 4 depicts a centerline, C, that bisects prosthetic finger 100 relative to a y-axis, and FIG. 5 shows a midline, M, that intersects a first hinged connection 110 and a second hinged connection 114, both detailed below, relative to a z-axis.

Turning to the various rotative connections shown in FIGS. 1-2, distal ring 104 may rotatively couple with coupling tip 106 via first hinged connection 110. First hinged connection 110 may include a pair of parallel pivotal hinges that are symmetric about centerline, C, discussed above in relation to FIG. 4. Each of the pivotal hinges of connection 110 may provide a pivot point between distal ring 104 and coupling tip 106.

Proximal ring 102 may rotatively couple with distal ring 104 via second hinged connection 114. Second hinged connection 114 may also include a pair of parallel pivotal hinges that are symmetric about the centerline, C, one located on each side of prosthetic finger 100 such that each provides a pivot point between proximal ring 102 and distal ring 104. As discussed above in relation to FIG. 5, the midline, M, intersects hinged connections 110 and 114, and, therefore, both first and second hinged connections 110, 114 are located directly upon the midline, M, relative to the z-axis.

Rocker 108 may form a H-shape having opposing first and second ends 116, 118, respectively, that extend between coupling tip 106 and proximal ring 102. First end 116 may form a first split prong of the H-shape and rotatively couple with coupling tip 106 via a third hinged connection 120 (FIGS. 1-2) located below the midline, M, relative to the z-axis. Second end 118 may form a second split prong of the H-shape and rotatively couple with proximal ring 102 via a fourth hinged connection 122 (FIGS. 1-2) located above the midline, M, relative to the z-axis. Both third and fourth hinged connections 120, 122 may include a pair of parallel pivotal hinges that are symmetric about the centerline, C, each providing a pivot point between rocker 108 and coupling tip 106/proximal ring 102.

Any one or more of the first, second, third, and/or fourth hinged connections 110, 114, 120, 122 may be outfitted with hard-stops to prevent hyperextension of finger 100 during operation. For example, a hard-stop 127, shown in FIG. 1, may prevent relative over-rotation of first hinged connection 110, or between distal ring 104 and coupling tip 106. Mechanical hard-stops may have any appropriate size, shape, and/or configuration.

Working together, proximal ring 102, distal ring 104, coupling tip 106, and H-shaped rocker 108 form a 4-bar linkage system that allows the coupling tip to be articulated in response to a pulling force on distal ring 104, which places the member in tension and reduces the risk of buckling. Thus, natural movement of the patient's residual finger seated within proximal ring 102 and distal ring 104, or in some cases movement of his or her adjacent fingers, may be used to actuate realistic flexion and extension motions within prosthetic finger 100. Users may perform their full range of usual activities, including typing, playing a musical instrument, or any other activity that requires the full dexterity of the hand.

The H-shape of rocker 108 allows third hinged connection 120 between rocker 108 and coupling tip 106 to occur outside the assembly, or outside the physical boundary defined by distal ring 104 and coupling tip 106. This configuration allows users with a relatively longer residual finger, or a relatively long middle phalanx, to take advantage of additional clearance space within the assembly. The residual finger may fit comfortably within the assembly, while still being protected against further damage and/or hypersensitivity. That said, while rocker 108 is described herein as having an H-shaped profile, it should be understood that rocker 108 may take any appropriate size, shape, type, and/or configuration.

In the embodiment shown in FIGS. 1-5, coupling tip 106 may include a tip pad 124. Tip pad 124 may be formed from a soft-textured silicone or other material that mimics the texture of a real finger. This aids with gripping and provides a softer touch. In one embodiment, a touchscreen mechanism (not shown) may be provided to allow the user to use the prosthetic finger to operate capacitive touchscreens, which react to the body's natural current. The touchscreen mechanism allows the user to direct his or her own body current through the tip of the prosthetic finger.

One embodiment of coupling tip 106 may also include a nail 126, which mimics a natural edged nail that may provide scratching and peeling functionalities as well as assist with fine-object manipulation.

Embodiments of prosthetic finger 100 are custom designed and individually fitted to accommodate a variety of differing user conditions, including different residual-finger lengths (e.g., varying amounts of loss to the finger). In this regard, each finger 100 may be customized to fit a particular patient or user, providing both custom functionality as well as a mechanical match to the anatomical joint articulation of the user, including matching the length of the original, non-amputated finger. Design considerations include an amount of finger loss, a number of joints to be replaced, and other characteristics specific to the individual end user. H-shaped rocker 108 is designed to provide a full-coverage "cage" above and about a patient's residual finger, thereby protecting the residual finger from irritation and/or hypersensitivity, without interfering with the residual finger within the prosthetic finger device 100. Outfitted with H-shaped rocker 108, a user may anchor any length of prosthetic finger within finger 100, even if the residual finger length extends well past the proximal interphalangeal ("PIP") joint. In cases in which the user has a fully formed, but poorly or nonfunctioning finger, coupling tip 106 may be removed so that prosthetic finger 100 functions as a joint brace, rather than a digit replacement.

To further provide better aesthetics, embodiments of finger 100 may be coated with films and/or colorings matched to the user's skin tone/color. An additive manufacturing process (i.e., 3D printing) facilitates this ability to customize the intricacies of the prosthetic finger design in order to optimize prosthetic finger 100 for each patient.

Embodiments of prosthetic finger 100 may be formed of any suitable structural material that is non-irritating to human skin and allows the user to operate the prosthetic with comfort and confidence. Exemplary materials include titanium, stainless steel, aluminum, silicone, carbon fiber, nylon, plastic/polymer, wood, rubber, gold, silver, tungsten, flex cable, neoprene, or any other suitable material. In one embodiment, components of prosthetic finger 100 are 3D printed from Duraform EX polymer material.

Using biocompatible materials, various embodiments of finger 100 may be applied as an orthopedic implant that may be surgically implanted into a user's finger. This option may be applied for users having injuries that have crushed their finger bones without the ability to heal or be repaired. In these situations, implantable embodiments of prosthetic finger 100 are able to take the place of the user's original bones without the need for amputation.

Figure 6:
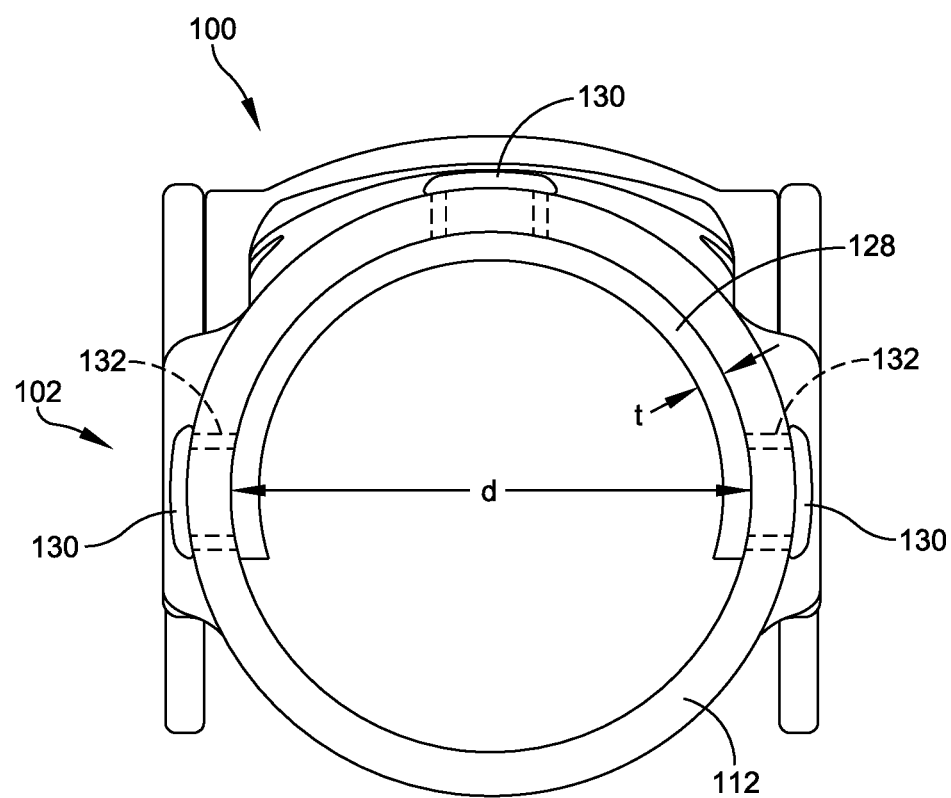
FIG. 6 illustrates an end view of the prosthetic finger assembly of FIGS. 1-5 with an inserted shim.

To use, the user may simply slide proximal ring 102 and distal ring 104 onto his or her residual finger, and, if necessary, adjust further using a shim(s). FIG. 6 depicts a rear view of prosthetic finger 100, in which body 112 of proximal ring 102 is outfitted with a semi-circular shim 128, which may be employed to allow the sizing of body 112 to account for possible swelling in the fingers, weight gain/loss, or any other post-manufacture changes in the size of the residual finger. In further detail, a fit kit (not shown) may be provided with each prosthetic finger 100 and may include a number of shims 128. In one embodiment, each shim 128 may approximate a semi-circle or U-shape configured to abut an inner diameter, d, of body 112 of proximal ring 102 and may have a number of retaining grommets 130 configured to protrude through corresponding shim-retainment apertures 132 within body 112. Each shim 128 may have a different thickness, t, thereby allowing the user to essentially adjust the inner diameter, d, of body 112 of proximal ring 102 in a number of increments as required by the user.

Once prosthetic finger 100 (adjusted or otherwise) is in place, the user can utilize his or her natural movements of the residual finger. The primary components of prosthetic finger 100 will articulate using the same cognitive process that was previously utilized for the original finger. If a user wears multiple fingers 100, each may be individually operated.

Figure 7:
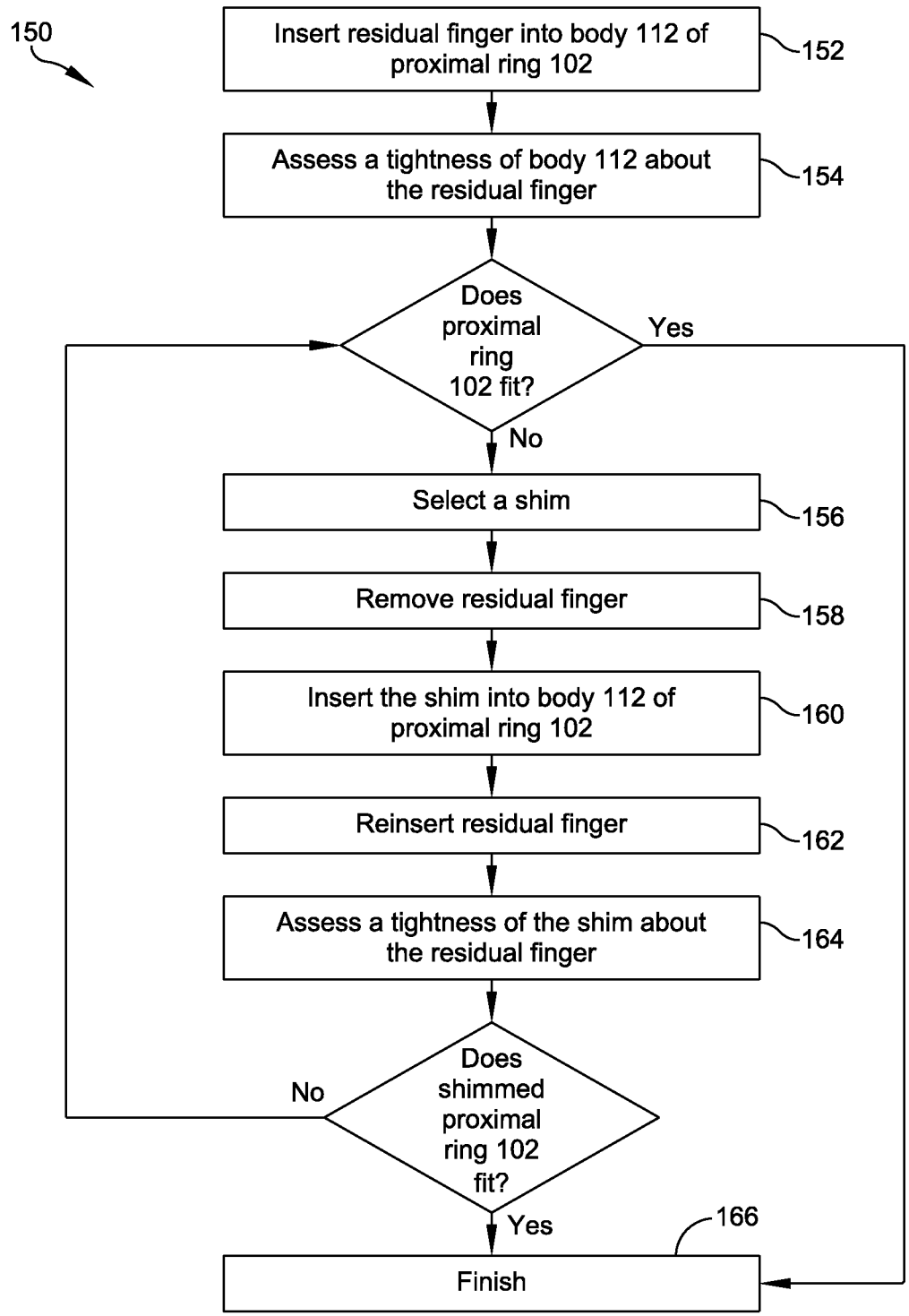
FIG. 7 illustrates a flow chart depicting an exemplary method of fitting the prosthetic finger assembly of FIGS. 1-6.

FIG. 7 provides a flow chart depicting an exemplary method 150 for installing and adjusting, or fitting, one embodiment of prosthetic finger 100 upon a user's residual finger. The method begins with inserting (152) the residual finger into body 112 of proximal ring 102 and assessing a tightness (154) of body 112 about the residual finger. Depending on this assessment (154), the user, a medical professional, or another assistant may select a first shim 128

(156) from the fit kit or another source. The user may then remove the residual finger (158) from proximal ring 102 and insert first shim 128 (160) into the inner diameter, d, of body 112 such that first shim 128 lines the inner diameter, d, while retaining grommets 130 protrude through shim-retainment apertures 132. Once first shim is installed (160), the user may reinsert the residual finger (162) into proximal ring 102 and assess a tightness (164) of first shim 128 (which now lines body 112 of proximal ring 102) about the residual finger. If the shimmed proximal ring 102 fits, method 150 is complete (166), and the user may proceed to biomechanically drive prosthetic finger 100. If shimmed proximal ring 102 does not fit, method 150 may return to the step of selecting a shim (156), in which a second shim having a different thickness may be selected before proceeding. The user may experiment with multiple shims of varying thicknesses until an ideal or desired fit is achieved. Of course, distal ring 104 may be adjusted in a manner similar to that discussed with respect to proximal ring 102 and method 150.

Figure 8:
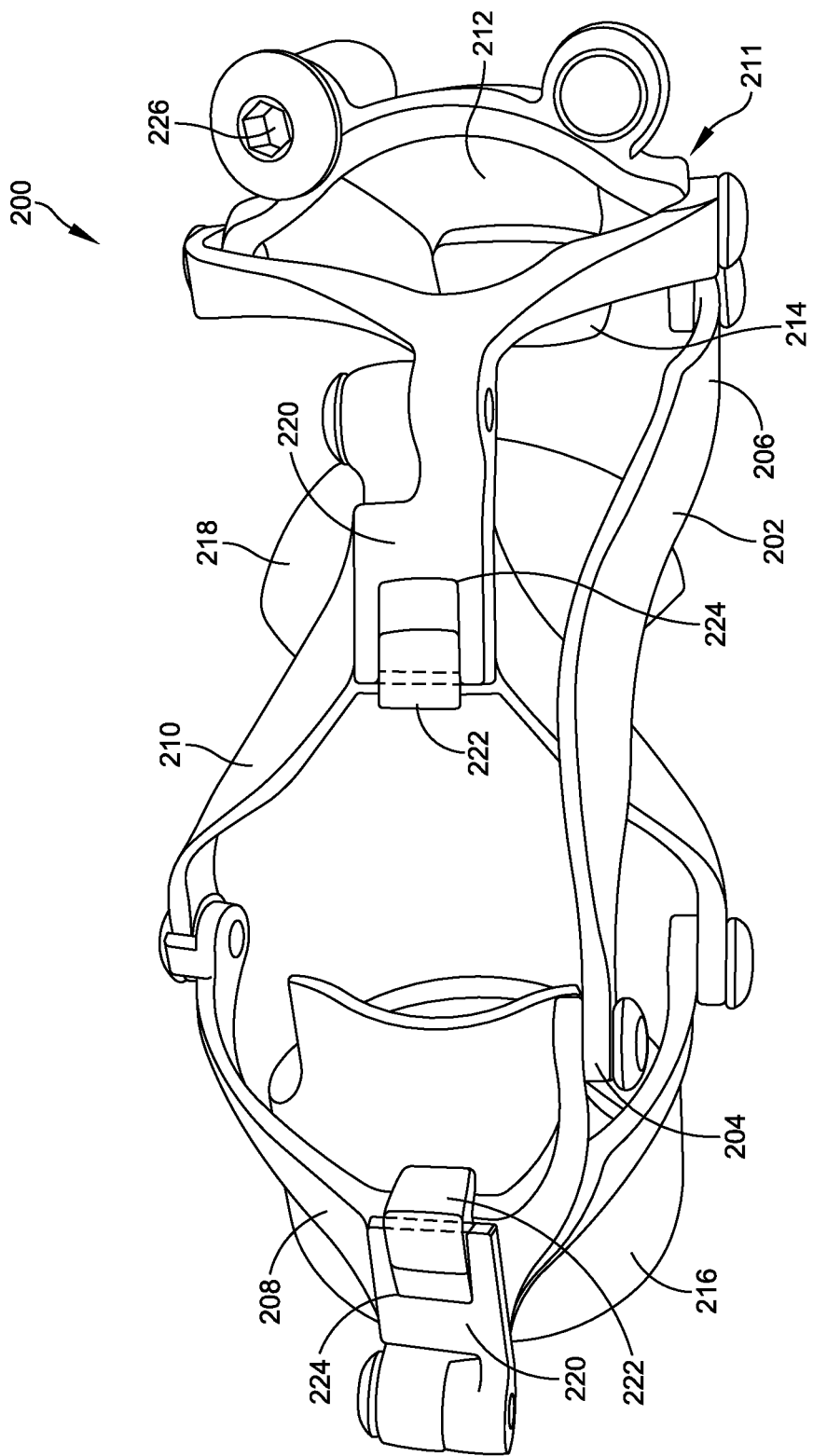
FIG. 8 illustrates a perspective view of one embodiment of a prosthetic finger device having a single rocker connecting a cupped receiving tip with a distal linkage and a proximal linkage.
Figure 9:
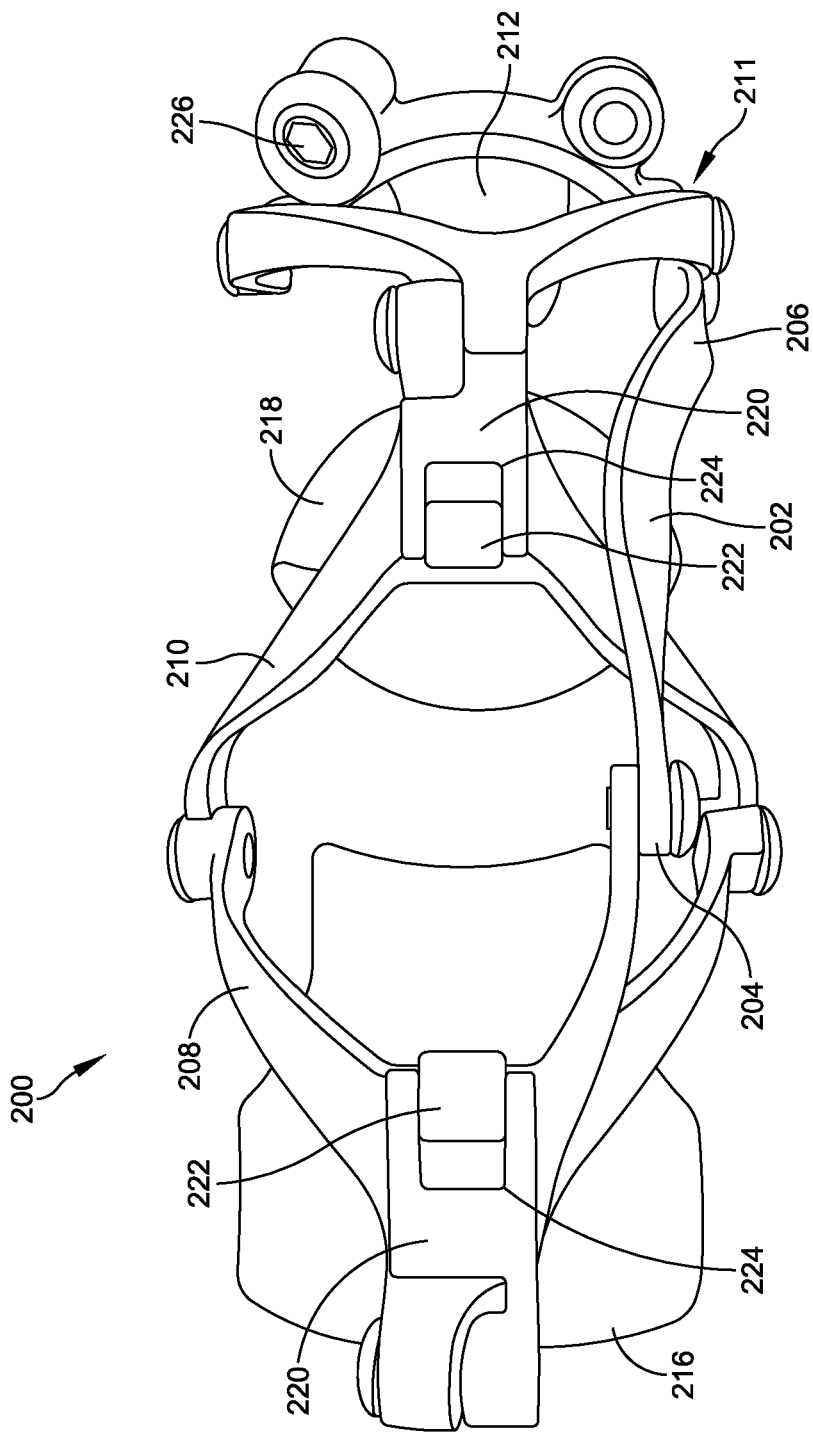
FIG. 9 illustrates a top view of the prosthetic finger device of FIG. 8.
Figure 10:
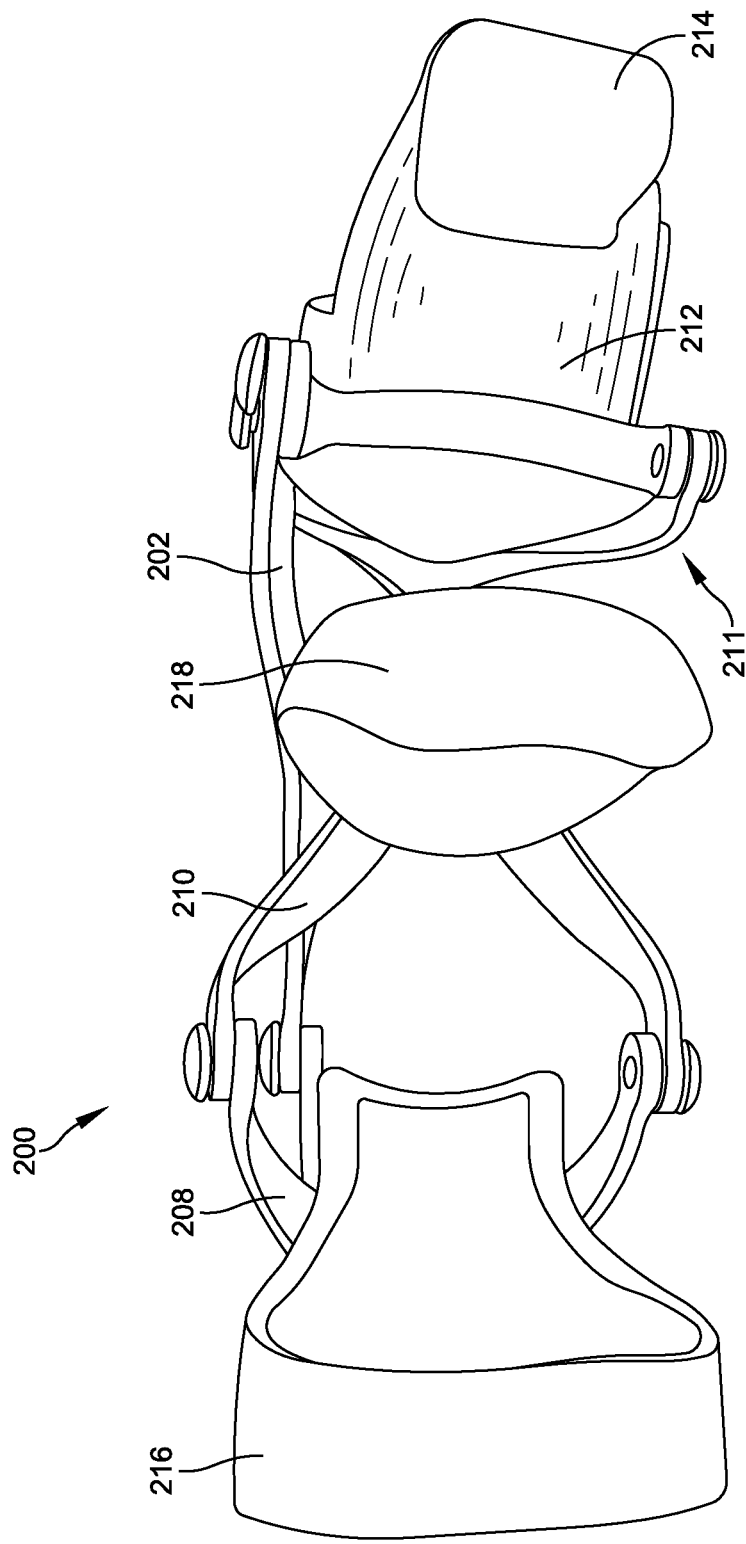
FIG. 10 illustrates a bottom view of the prosthetic finger device of FIGS. 8-9.
Figure 11:
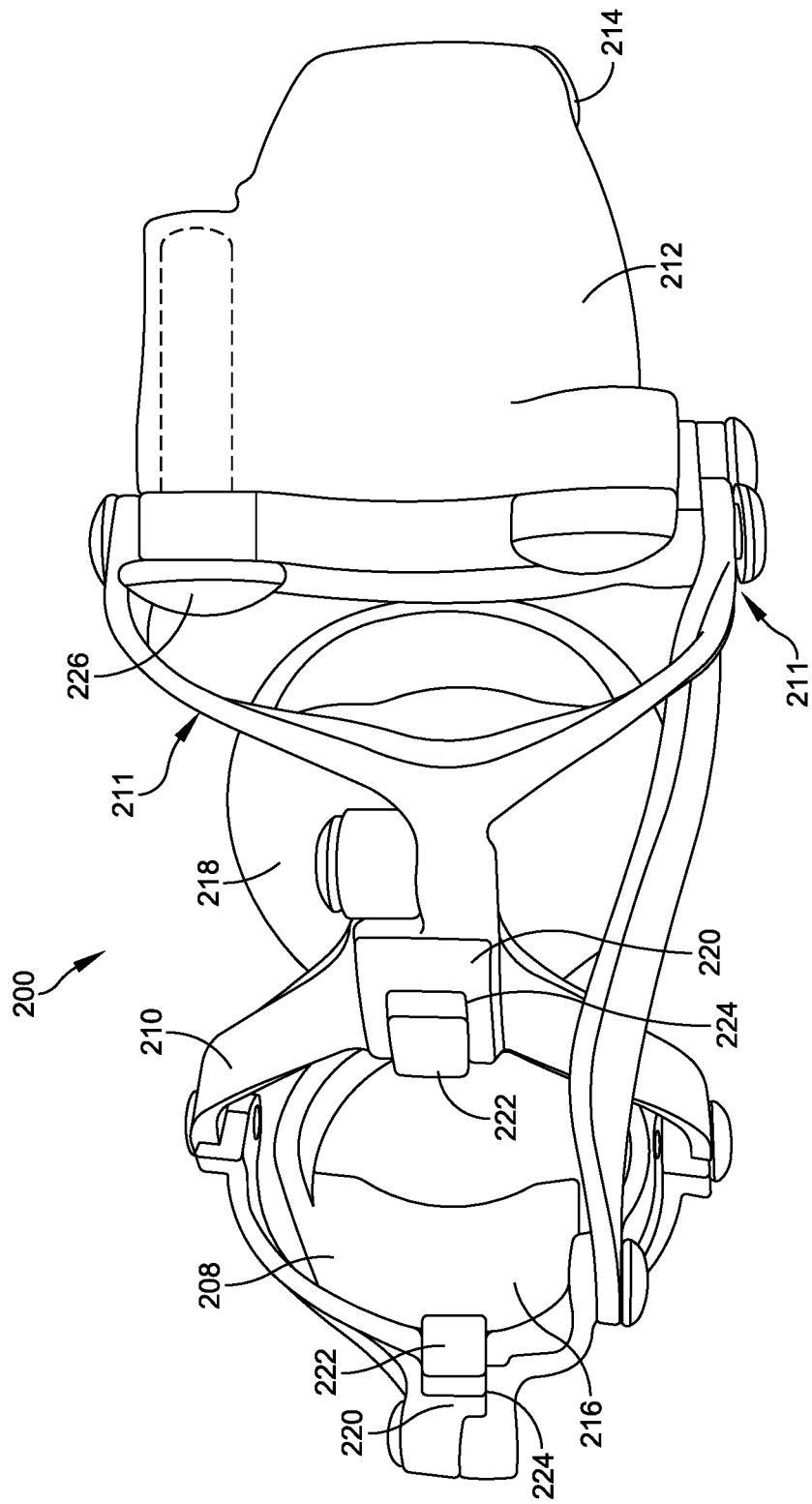
FIG. 11 illustrates another perspective view of the prosthetic finger device of FIGS. 8-10 with the cupped receiving tip in an extended position.

FIGS. 8-11 illustrate first perspective, top, bottom, and second perspective views of an alternate embodiment of a prosthetic finger 200. In this embodiment, prosthetic finger 200 includes three primary interlinked components: a rocker 202 having a proximal end 204 and a distal end 206, a proximal linkage 208, and a distal linkage 210. In further detail, and as shown in FIGS. 8-9, distal linkage 210 may rotatively couple with proximal linkage 208, which may, in turn, couple with proximal end 204 of rocker 202. Distal end 206 of rocker 202 may rotatively couple with a swiveling tip brace 211. Swiveling tip brace 211 may feature a tip fastener joint 226, shown in FIGS. 8-9 and 11, that allows a receiving tip 212 to be positioned at varying angles relative to swiveling tip brace 211 and to the remainder of prosthetic finger 200 in order to achieve different grip strengths and/or articulation characteristics. A tip pad 214 may attach to tip 212 in any appropriate manner.

Two cage rings may attach to the linkages for the purpose of retaining a user's residual finger (with one ring proximal of the proximal interphalangeal ("PIP") joint and another ring distal of the PIP joint) and translating movement of the residual finger through the interlinked assembly discussed above. As shown in FIGS. 6-9, a proximal cage ring 216 and a distal cage ring 218 may attach to proximal linkage 208 and distal linkage 210, respectively. This attachment may be facilitated by a universal ring mount 220 located on each of proximal linkage 208 and distal linkage 210. Each universal ring mount 220 may define a ring mount aperture 224 that is configured to receive an attachment protrusion 222 of each of cage rings 216, 218.

In use, a user/patient may slide proximal and distal cage rings 216, 218 of prosthetic finger 200 over his or her residual finger like a ring. Each finger 200 may be customized to fit the particular user in question. As a result, rocker 202, proximal and distal linkages 208, 210, and/or swiveling tip brace 211 may be customized to accommodate the length of the user's residual finger or other physical characteristic of the particular user, such that when prosthetic finger 200 is anchored to the user's residual finger, an end or tip of the residual finger may nest within or adjacent to receiving tip 212. In one embodiment, receiving tip 212 may be curved or "cupped" to receive the residual finger end or tip in a manner that protects the user's finger from further damage and/or hypersensitivity. The components of prosthetic finger 200 not only look realistic during articulation, but receiving tip 212, with a residual finger end or tip nested therein, bends in a realistic manner as rocker 202 is articulated.

While prosthetic finger 200 may be custom designed to custom fit each user, post-manufacturing changes to the patient's physiology may occur. To add post-manufacturing customization capabilities to prosthetic finger 200, both proximal cage ring 216 and distal cage ring 218 may be interchangeable such that they may be swapped out with rings of varying sizes to address sizing and/or swelling fluctuations demonstrated in the residual finger of the patient. Varying sizes of proximal and distal cage rings 216, 218 may be provided in a fit kit (not shown), allowing the user to employ the most appropriate ring sizes in real-time. The user may easily interchange cage rings by removing the rings 216, 218 from, and replacing different rings to, ring mounts 220 via ring mount apertures 224 and attachment protrusions 222. Interchangeable rings 216, 218 may be formed of any appropriate material including flexible polymers or other plastics that are non-irritating to human skin.

Embodiments of the prosthetic fingers 100, 200 described above exhibit numerous unique characteristics and provide a variety of medical benefits. An individual's unique physiology and lifestyle patterns dictate the function and performance expected of his or her hands. Using embodiments of the prosthetic fingers described herein, patients may regain independent control of their hands, whether at work or at play. Each device is custom designed, manufactured for a specific individual, and incorporates features that allow for further fine-tuning and adjustment of fit to account for post-manufacturing fluctuations (e.g., shims and or interchangeable rings), enabling the device to fit the user in a manner that allows for a biomechanically driven, low profile, lightweight, highly functioning return to the user's everyday activities, no matter what those activities might entail. A few examples include typing, playing the piano or another instrument, woodworking, and much more.

Embodiments of the prosthetic fingers described above are body powered, and their linked components articulate when the user simply moves his or her residual finger, when available, or an adjacent finger when necessary. Beyond allowing for a simple, elegant, and streamlined design that offers strength in the lowest possible profile design, employing the user's own biomechanics to drive embodiments of prosthetic fingers 100, 200 provides a host of medical benefits to the user, including reduced swelling of and increased circulation to the residual finger and the hand as a whole, supporting healthy joints in the injured and adjacent fingers.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A method of fitting a customized prosthetic finger having a proximal ring configured to anchor to a patient's residual finger, the proximal ring containing one or more shim-retainment apertures, comprising:

inserting the residual finger into an interior of the proximal ring of the prosthetic finger;

assessing a tightness of the proximal ring about the residual finger;

selecting a first shim having a first thickness from a plurality of shims configured to line the interior of the proximal ring, each of the shims including one or more retaining grommets;
removing the prosthetic finger;
inserting the first shim into the interior of the proximal ring such that the retaining grommets protrude through the shim-retainment apertures, thereby retaining the first shim within the interior of the proximal ring; and
reinserting the residual finger.

2. The method of claim 1, further comprising:
assessing a tightness of the first shim about the residual finger;
removing the prosthetic finger;
removing the first shim;
selecting, from the plurality of shims, a second shim having a second thickness; and
inserting the second shim into the interior of the proximal ring such that the retaining grommets protrude through the shim-retainment apertures, thereby retaining the second shim within the interior of the proximal ring.

3. The method of claim 1, wherein each of the plurality of shims has a different thickness.

4. The method of claim 3, wherein the interior of the proximal ring has an inner diameter, and wherein each of the plurality of shims reduces the inner diameter of the proximal ring by an amount proportional to each of the different thicknesses, respectively.

5. The method of claim 1, wherein each of the plurality of shims has a shape that approximates a U-shape.

6. A method of installing a prosthetic device onto a user's residual finger, comprising:
providing a customizable prosthetic finger having a proximal ring configured to concentrically receive the user's residual finger, the proximal ring forming at least one shim-retainment aperture;
inserting the residual finger into an interior of the proximal ring of the customizable prosthetic finger;
assessing a fit of the proximal ring about the residual finger;
removing the customizable prosthetic finger from the residual finger;
providing a plurality of shims, each of the plurality of the shims including at least one retaining grommet and configured to be received within the interior of the proximal ring, wherein each of the plurality of the shims has a different thickness;
selecting a first shim having a first thickness from the plurality of the shims;
inserting the first shim into the interior of the proximal ring such that the first shim reduces an inner diameter of the interior of the proximal ring by an amount proportional to the first thickness, wherein the inserting the first shim into the interior of the proximal ring comprises inserting the at least one retaining grommet into the at least one shim-retainment aperture such that the at least one retaining grommet protrudes through the at least one shim-retainment aperture, thereby retaining the first shim within the interior of the proximal ring; and
reinserting the residual finger into the interior of the proximal ring.

7. The method of claim 6, further comprising:
assessing a fit of the first shim about the residual finger;
removing the customizable prosthetic finger from the residual finger;
selecting a second shim having a second thickness from the plurality of the shims;
replacing the first shim with the second shim within the interior of the proximal ring such that the second shim reduces the inner diameter of the interior of the proximal ring by an amount proportional to the second thickness; and
reinserting the residual finger into the interior of the proximal ring.

8. The method of claim 7, further comprising:
assessing a fit of the second shim about the residual finger;
removing the customizable prosthetic finger from the residual finger;
selecting a third shim having a third thickness from the plurality of the shims; and
replacing the second shim with the third shim within the interior of the proximal ring such that the third shim reduces the inner diameter of the interior of the proximal ring by an amount proportional to the third thickness.

9. The method of claim 6, wherein each of the plurality of the shims has a shape that approximates a semi-circle.

10. A method of adjusting a customizable prosthetic finger to fit a user's residual finger, the customizable prosthetic finger including a proximal ring having an interior configured to concentrically receive the residual finger and forming at least one shim-retainment aperture, the method comprising:
(1) selecting a fit shim from a plurality of fit shims, each of the plurality of the fit shims including at least one retaining grommet;
(2) inserting the selected fit shim into the interior of the proximal ring such that the fit shim reduces an inner diameter of the interior of the proximal ring by an amount proportional to the selected fit shim, wherein the inserting the selected fit shim into the interior of the proximal ring comprises inserting the at least one retaining grommet into the at least one shim-retainment aperture such that the at least one retaining grommet protrudes through the at least one shim-retainment aperture, thereby retaining the selected fit shim within the interior of the proximal ring;
(3) inserting the residual finger into the proximal ring of the customizable prosthetic finger; and
(4) assessing a tightness of the selected fit shim about the residual finger.

11. The method of claim 10, further comprising:
(5) removing the customizable prosthetic finger from the residual finger;
(6) removing the selected fit shim from the interior of the proximal ring; and
(7) iteratively repeating the steps (1) through (6) until the proximal ring and the selected fit shim anchor about the residual finger with a snug fit.

12. The method of claim 11, wherein each of the plurality of the fit shims has a different thickness.

13. The method of claim 10, wherein each of the plurality of the fit shims has a shape that approximates a U-shape.

* * * * *